United States Patent [19]
Hirt et al.

[11] Patent Number: 5,902,733
[45] Date of Patent: May 11, 1999

[54] TEST SYSTEM FOR DETERMINING THE ACTIVITY OF NATURAL KILLER CELLS

[75] Inventors: Werner Hirt, Heidelberg; Volker Ehemann, Walldorf; Alexander Wink, Heidelberg, all of Germany

[73] Assignee: Orpegen Pharma GmbH, Heidelberg, Germany

[21] Appl. No.: 08/945,470

[22] PCT Filed: Jan. 17, 1996

[86] PCT No.: PCT/EP96/00186

§ 371 Date: Feb. 17, 1998

§ 102(e) Date: Feb. 17, 1998

[87] PCT Pub. No.: WO96/41163

PCT Pub. Date: Dec. 19, 1996

[30] Foreign Application Priority Data

Jun. 7, 1995 [DE] Germany ............. 195 20 729

[51] Int. Cl.$^6$ .............. C12Q 1/02; C12Q 1/00; G01N 33/53
[52] U.S. Cl. .................. 435/29; 435/4; 435/1.1; 435/1.3; 435/968; 435/975; 435/973; 435/7.1; 435/7.2; 435/7.21; 435/7.23; 435/7.24
[58] Field of Search ................ 435/29, 4, 1.1, 435/1.3, 968, 975, 973, 7.1, 7.2, 7.21, 7.23, 7.24

[56] References Cited

U.S. PATENT DOCUMENTS 4,983,515  1/1991  Maley et al. ............. 435/29

FOREIGN PATENT DOCUMENTS 9009432  8/1990  WIPO.

OTHER PUBLICATIONS

H.T. Holden et al., "Standardization of the Chromium-51 Release, Cell-Mediated Cytotoxicity Assay: Cryopreservation of Mouse Effector and Targeted Cells," *Journal of the National Cancer Institute*, 58(3):611–622 (Mar. 1, 1977).

*Primary Examiner*—Louise N. Leary
*Attorney, Agent, or Firm*—Fulbright & Jaworski, LLP.

[57] ABSTRACT

The invention concerns a method for determining the action of effectors on target cells, wherein thawed cryopreserved mammalian cells are used without prior culture as target cells which have a vitality of at least 85% after storage at −70° C. for a period of 4 weeks and are obtainable by preparing a suspension of the target cells in a medium, adding a cryopreservative up to a final concentration of 2–10% (v/v) and freezing the cells with a temperature decrease of no more than 2° C. per minute.

22 Claims, 6 Drawing Sheets

SC/SSC-dot plot of K562 target cells

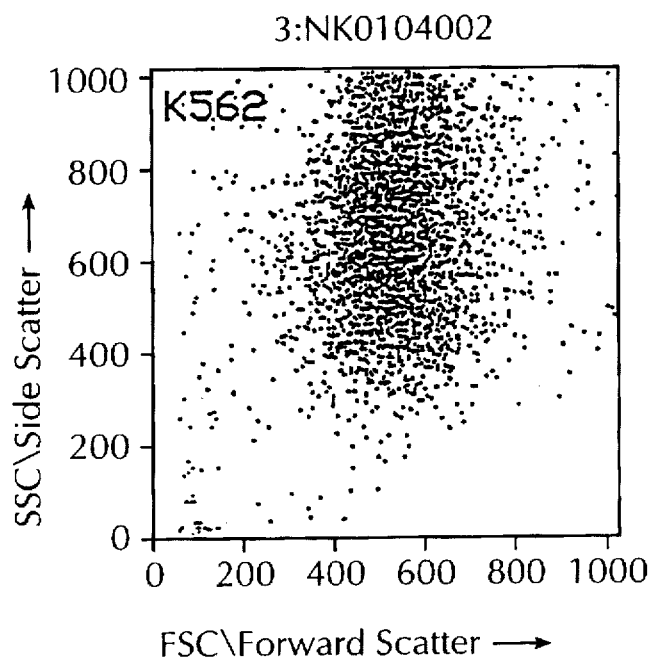
FIG. 1: SC/SSC-dot plot of K562 target cells
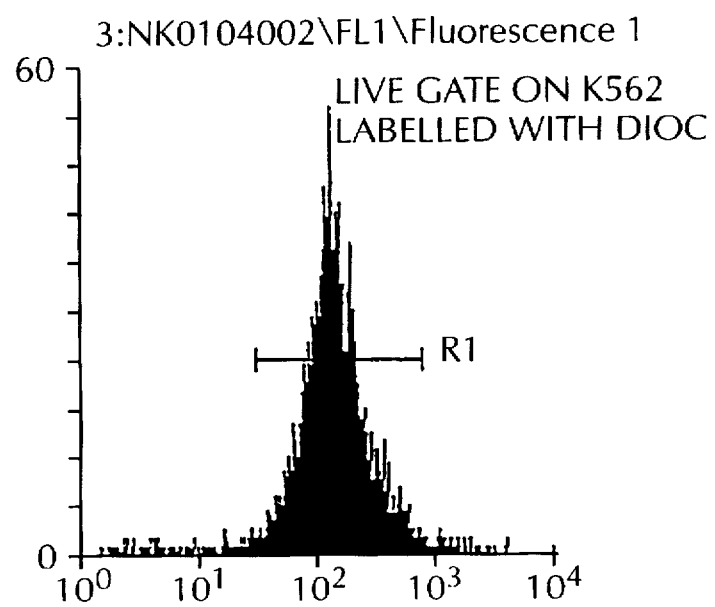
FIG. 2: green fluorescence of labelled K562

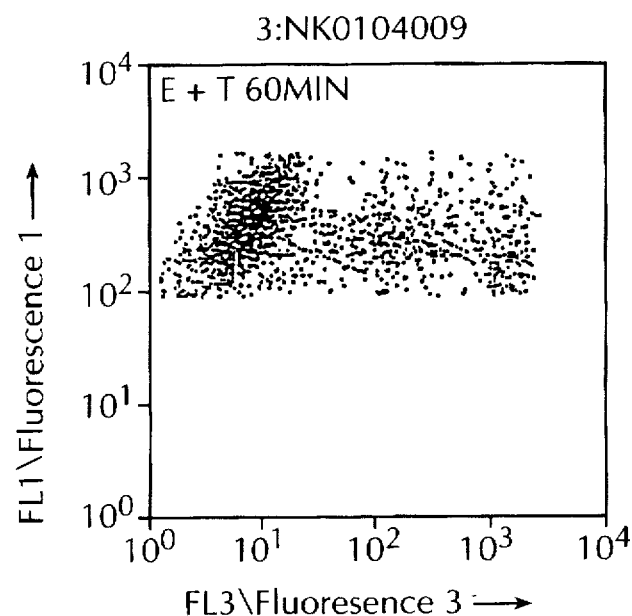
FIG. 3: FL3/FL1-dot blot of targets (incubated for 30 min with effectors)
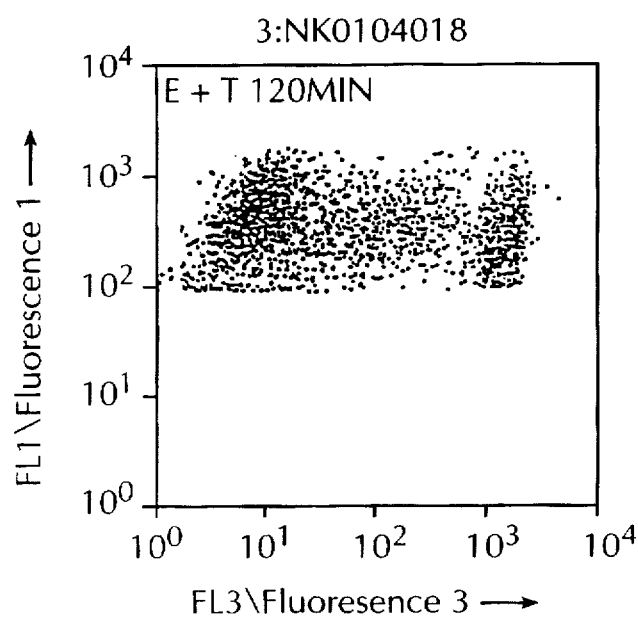
FIG. 4: L3/FL1-dot blot of targets (incubated for 120 min effectors)

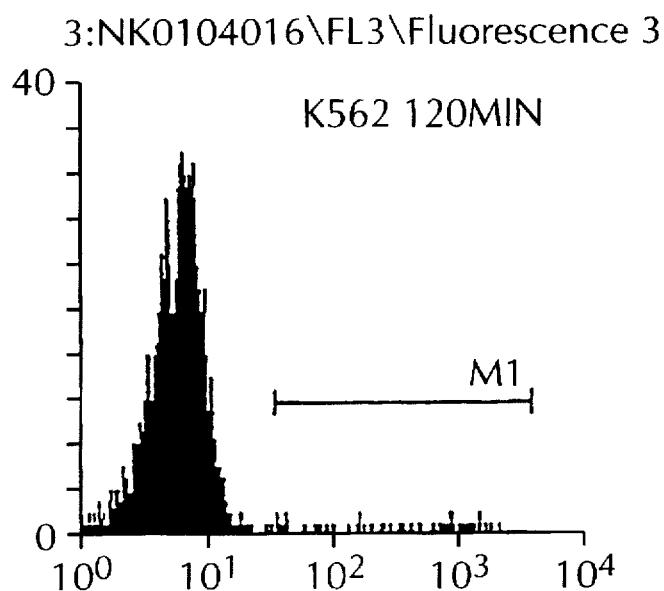
FIG. 5: FL3 histogram of the target cells (incubation 120 min)
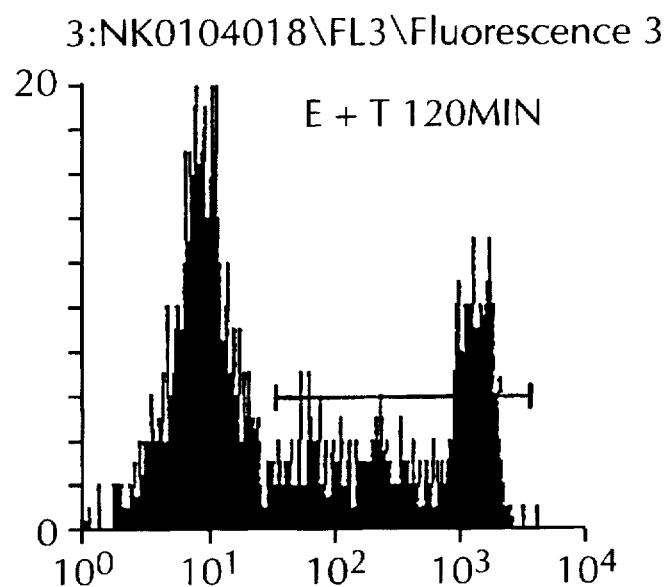
FIG. 6: FL3 histogram of the target cells with effectors (incubation 120 min)

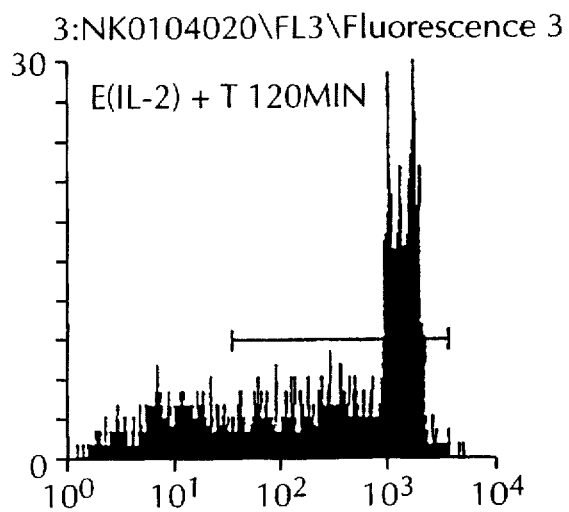
FIG. 7: FL3 histogram of target cells with IL-2-stimulated effectors (incubation 120 min)
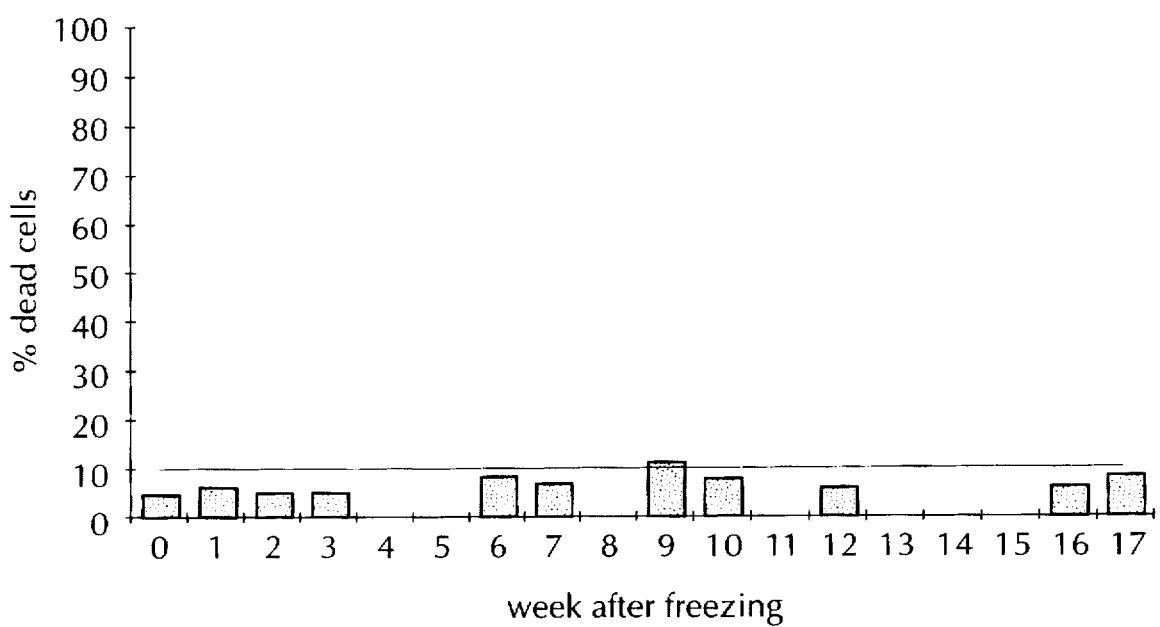
FIG. 8

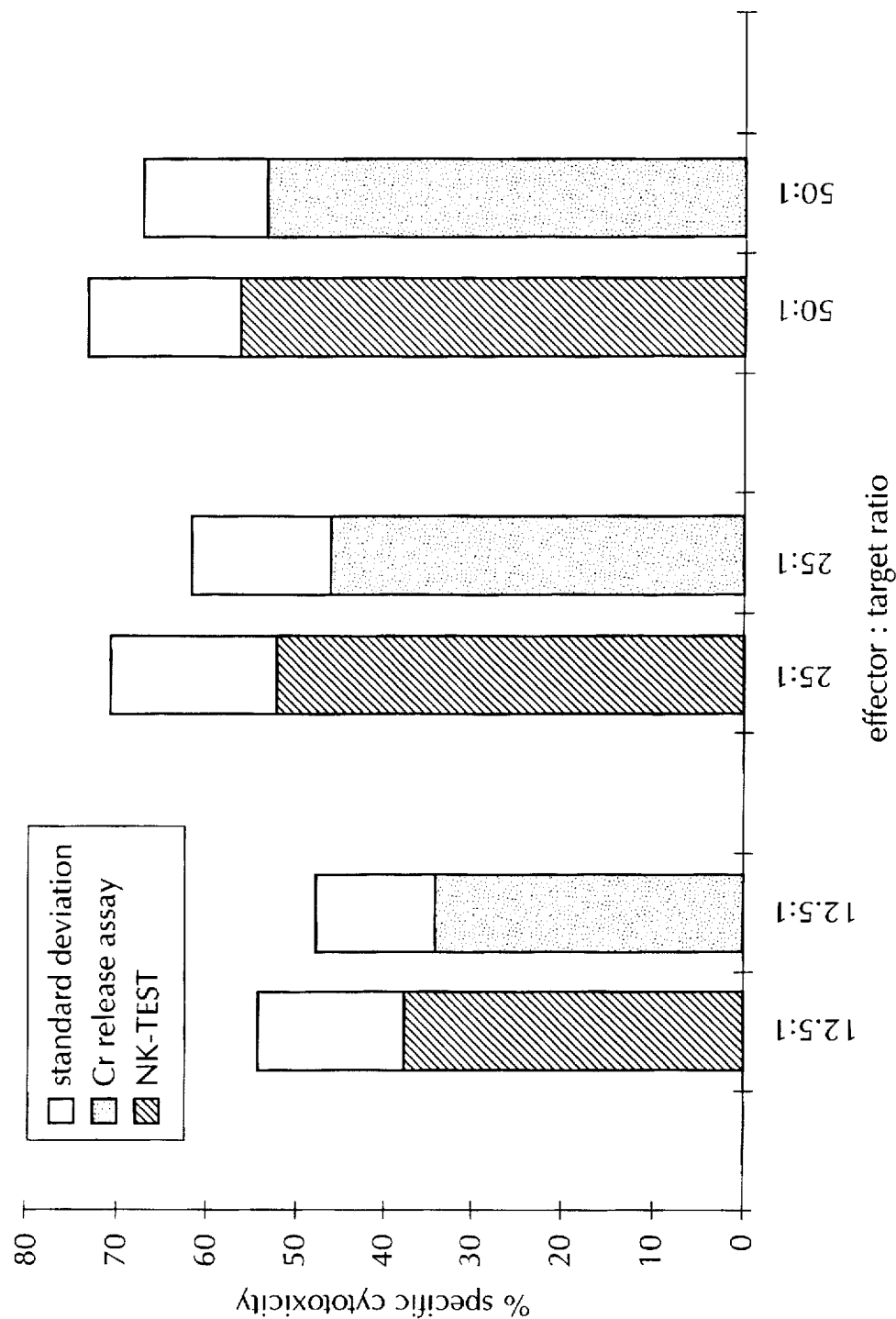

TEST SYSTEM FOR DETERMINING THE ACTIVITY OF NATURAL KILLER CELLS

The present invention concerns a method to determine the action of effectors on target cells in particular the activity of natural killer cells (NK cells) as well as a suitable reagent kit for this.

NK cells play an important role in the immune system of mammals and are defined by their function as immune cells which exhibit a spontaneous non-MHC-restricted cytotoxic activity towards numerous target cells such as tumour cells, virus-infected cells or allogenic target cells. The morphological majority of these effectors of natural cell-mediated immunity are large granulated lymphocytes and are defined immunophenotypically as CD3 negative lymphocytes which express CD56 and/or CD16. A small number of T lymphocytes ($CD3^+CD56^+$) also exhibit NK activity.

A reduced NK activity was found in patients with AIDS, "AIDS related complex" (ARC) [Bonavida, B. et al. 1986, J. Immunol. 137: 1157–1163, Brenner B. et al. 1989, J. Leuk. Biol. 46: 75–83, Quan, C. et al. 1990, J. Acq. Immune Deficiency Syndromes 3: 669–676], patients with Down's syndrome [Cossarizza, A. et al. 1991, Blood 77: 1263–1270] as well as in patients with chronic fatigue syndrome [Caligiurri, M. et al. 1987, J. Immunol. 139: 3306–3313, Klimas, N. et al. 1990, J. Clin. Microbiol. 28: 1403–1410, Landay, A. et al. 1991, Lancet 338: 707–713]. In addition the NK cell activity is increased during a virus infection [Trinchieri, G. 1989, Adv. Immunol. 47: 187–376]. Patients in an advanced stage of cancer usually exhibit a reduced NK cell activity [Kadish, A. S. et al. 1981, J. Immunol. 127: 1817, Takasugi, M. et al. 1977, Cancer Res. 37: 413].

The previous most common assay for the determination of the cytotoxic activity of NK cells is the $^{51}Cr$ release assay [Brunner, K. T. et al. 1968, Immunology 14:18]. However, this method has several important disadvantages for a broad application in routine diagnostics and namely the necessity of a specially equipped isotope laboratory, the use of a radioactive isotope with a relatively short half-life, high costs, a relatively high spontaneous release of $^{51}Cr$ and long labelling and incubation periods.

Other methods for the quantification of cytotoxicity have been described and comprise the measurement of released substances such as e.g. fluorescent dyes (Europium [Blomberg, K. et al. 1986, J. Immunol. Methods 86: 225] or H33342 [Brenan, M. 1988, J. Immunol. Methods 112:121]) or the determination of the enzyme activity of released cytoplasmic enzymes [Korzeniewski, C. 1983, J. Immunol. 64: 313].

In addition flow cytometric methods have been described for the determination of NK effector activity which enable the cytotoxicity to be observed at a single cell level [McGinnes, K. et al. 1986, J. Immunol. Methods 86: 7–15, Zarzone, D. et al. 1986, J. Immunol. Methods 94: 247–255, Papa, S. et al. 1988, J. Immunol. Methods 107: 73–78]. However, a disadvantage of these methods is that they cannot unequivocally differentiate between target and effector cells. Therefore flow cytometric methods have been developed in which the membranes of the target cells are labelled with fluorescent dyes to differentiate them from effector cells [Slezak, S. E. et al. 1989, J. Immunol. Methods 117: 205–214, Radosevic, K. et al. 1990; J. Immunol. Methods 135: 81–89].

Kroesen, B.-J. et al. [J. Immunol. Methods 156 (1992): 47–54] and Chang, L. et al. [J. Immunol. Methods 166 (1993): 45–54] describe a method for the determination of NK activity using the lipophilic membrane dye 3,3'-dioctadecyloxacarbocyanine perchlorate ($DiOC_{18}$). The NK-sensitive human erythromyelocytic leukemia cell line K562 [Lozzio, B. B. et a. 1976, J. Natl. Cancer Inst. (U.S.) 56: 627] kept in cell culture was used as target cells.

A disadvantage of the previously described methods is the necessity to culture the target cells in a cell culture laboratory before actually carrying out the assay.

Therefore an object of the present invention was to develop a method in which the disadvantages of the state of the art are at least partially eliminated. In particular it was intended to develop a method for the cryopreservation of cells in which the cells can be stored at $-70°$ C. without loss of vitality and can thus be used directly without prior culture in a diagnostic test e.g. the flow cytometric NK test.

This object is achieved by a method for the determination of the action of effectors on target cells which is characterized in that thawed cryopreserved mammalian cells are used without prior culture as target cells which have a vitality of at least 85% after storage at $-70°$ C. over a period of 4 weeks and which are obtainable by preparing a suspension of the target cells in a medium, adding a cryopreservative to a final concentration of 2–10% (v/v) and freezing the cells with a temperature decrease of no more than $2°$ C. per minute. The freezing is preferably carried out down to a temperature of at least $-50°$ C. particularly preferably of at least $-65°$ C. and most preferably of about $-70°$ C. in order to gently cryopreserve the target cells while retaining their vitality. It was surprisingly found that the cryopreserved cells have a sufficiently high vitality to be suitable for use as target cells in clinical diagnostics. Target cells are preferably used which are derived from a cell culture in particular a human cell line. Human tumour or leukemia cell lines are particularly preferred. The cell lines are most preferably selected from the chronic myelogenic leukemia cell line K562 (ATCC CCL 243), the acute lymphoblastic leukemia T cell line MOLT-4, the acute promyelocytic leukemia cell line HL-60, the ovarian carcinoma cell line Goodwin and the alveolar cell carcinoma cell line A549. Reference is made to Pross et al. (J. Clin. Immunol. 1 (1981), 51–63) and the literature references cited therein with regard to these cell lines and their use as target cells in NK assays.

Preferably cells are used from a cell culture in the exponential growth phase. After harvesting these cells are adjusted to a concentration of $1\times10^5$ to $5\times10^6$/ml particularly preferably about $1\times10^6$/ml, brought to a temperature of $0-4°$ C. by cooling and admixed with the cryopreservative. The final concentration of the cryopreservative in the medium is preferably 4–8% (v/v), particularly preferably about 5%. Dimethylsulfoxide (DMSO) or glycerol are preferably used as cryopreservatives. DMSO is particularly preferably used.

The cells are frozen with a temperature decrease of no more than $2°$ C. per minute, preferably with a temperature decrease of $0.5-1.5°$ C. per minute and particularly preferably with a temperature decrease of about $1°$ C. per minute.

Cryopreserved mammalian cells are obtainable by the method according to the invention which still have a vitality of at least 85% and preferably of at least 90% after storage for a period of 4 weeks and preferably of 12 weeks. In this connection a vitality of at least 85% means that after freezing and thawing at least 85% of the cells that were viable before freezing are still viable. The vitality of the cells can be determined by known methods e.g. a dye exclusion test using trypan blue or erythrocin B. In this dye exclusion test a solution of dye is added to the cells and the number of dead cells which cannot take up the dye is determined in relation to the total number of tested cells.

The method according to the invention concerns a determination of the action of effectors on target cells. The effectors may be chemical or biological substances, cells, microorganisms or combinations thereof. Preferably cells and in particular natural killer cells are used as effectors.

An important feature of the method according to the invention is that the test can be carried out without prior culture of the target cells, the target cells can be thawed immediately before carrying out the assay. This means that the target cells are used in the assay within a maximum period of preferably 8 h, particularly preferably within a maximum of 2 h and most preferably within a maximum of 1 h after thawing. Hence the assay can be carried out with standardized target cells. This is a prerequisite for an application in routine diagnostics. Consequently it was necessary to establish a method which cryopreserves the cells as mildly as possible while retaining their vitality. For this purpose K562 cells were for example harvested in the log phase for a NK test, adjusted to a concentration of $1 \times 10^6$ ml and admixed with DMSO to a final concentration of 5% (v/v). The cells are frozen at $-70°$ C. with a temperature decrease of $1°$ C. per minute. The cells are stored at $-70°$ C. in a deep freezer.

In order to differentiate between effector cells and target cells, the target cells are preferably labelled. On the one hand the target cells can be labelled after thawing preferably without prior culture. On the other hand it was surprisingly found that it is possible to label the target cells even before the cryopreservation. This procedure has the advantage that the already labelled target cells can be used directly in the assay after thawing.

In a first preferred embodiment of the method according to the invention the activity of NK cells can be determined by labelling the cryopreserved target cells after thawing with a first marker substance, mixing and incubating them with a sample containing NK cells, specifically labelling the killed target cells with a second marker substance and determining the marker. According to a second preferred embodiment the target cells are labelled before the cryopreservation with a first marker substance, mixed and incubated after thawing without prior culture with a sample containing NK cells, the killed target cells are specifically labelled with a second marker substance and the marker is determined.

The first and second marker substance are selected so that they can be detected concurrently.

A membrane dye is preferably used as a first marker substance to label the target cells. A lipophilic fluorescent dye is preferably used such as 3,3'-dioctadecyloxacarbocyanine perchlorate ($DiOC_{18}$) [Bradley, R. A. et al. 1973, Biochemistry 12: 268]. The use of $DiOC_{18}$ to label K562 target cells in the NK assay has already been described [Kroesen, B.-J. et al., J. Immunol. Methods 156 (1992): 47–54; Chang, L. et al., J. Immunol. Methods 166 (1993): 45–54].

The membrane dye $DiOC_{18}$ is preferably dissolved at a concentration of 0.5–2 mg/ml, in particular ca. 1.25 mg/ml (1.42 mM) in dimethylsulfoxide. For the staining 20 µl of this stock solution is added to ca. $1 \times 10^6$ target cells in 5 ml complete medium. This results in a final concentration of 4.85 µg/ml and a DMSO concentration of 0.4% (v/v). This at the same time avoids a concentration of organic solvent which is too high and toxic for the cells. For the staining the cells are subsequently incubated at $37°$ C. for preferably 5–30 min, e.g. 15 min, with the membrane dye and subsequently washed once with complete medium (120 g, 3 min).

Mononuclear effector cells are isolated by standard methods (density gradient centrifugation over Ficoll or by means of leuko-PREP cell separation tubes 13 mm or 16 mm (Becton Dickinson), from blood e.g. heparinized or citrate whole blood. The presence of monocytes in the test preparations can reduce the cytotoxic activity of the NK cells. The NK activity of the isolated lymphocytes can therefore be increased by depleting the monocytes. Non-adherent effector cells can be concentrated for example by a plastic adherence step or by passage through nylon wool.

In a preferred embodiment of the method according to the invention duplicate determinations are carried out in each case with various ratios of effectors to target cells. The ratios 50:1, 25:1 and 12.5:1 are preferably used. In order to bring the effector and target cells into close contact the cell suspensions are briefly centrifuged (100 g, 1 min). The incubation period of the effector cells with the target cells can be 30 to 240, min preferably 120 min. However, it is also possible to carry out the method according to the invention in several parallel preparations with various incubation periods.

The NK effector activity can be increased by immunomodulators such as e.g. interleukin 2 or interferon-alpha. In a preferred embodiment of the method according to the invention two parallel preparations are carried out in which one of these preparations additionally contains interleukin 2 at a concentration of 30 U/ml.

The dead target cells are stained by adding a second marker preferably a DNA dye e.g. a fluorescent DNA dye. A dye which is known to be suitable for this purpose can be used as a DNA dye which has a different emission wavelength than that of the first dye used to label the membranes of the target cells. Propidium iodide is preferably used as the DNA dye.

The last step of the method according to the invention is to determine the label e.g. the fluorescence. It can be determined by means of a flow cytometer or a microscope.

A further subject matter of the present invention is a reagent kit especially for the determination of the NK effector activity of human peripheral lymphocytes. In a first embodiment the kit contains a membrane dye, a DNA dye and cryopreserved target cells that are physically separated from one another. In a second embodiment the kit contains cryopreserved target cells labelled with a membrane dye and a DNA dye which are physically separated from one another. The reagent kit preferably also contains a medium for the cell culture or/and a modulator for NK cells e.g. a stimulant such as interleukin 2. The components of the reagent kit may be ready-to-use solutions or lyophilisates from which the user first reconstitutes the solutions. In a particularly preferred design of the first embodiment according to the invention the reagent kit contains the following components:

1. Cryopreserved K562 target cells
2. Solution of the lipophilic membrane dye 3,3'-dioctadecyloxacarbocyanine perchlorate ($DiOC_{18}$) in dimethyl sulfoxide
3. Complete medium composed of the cell culture medium RPMI 1640 and 10% (v/v) FCS
4. DNA dye solution containing propidium iodide and preservative In a particularly preferred design of the second embodiment the kit contains cryopreserved target cells that are already labelled with $DiOC_8$ instead of the above components 1 and 2.

A flow cytometer (e.g. FACScan, Becton Dickinson Co.) with a 488 nm light excitation (argon laser) is preferably used as the measuring instrument.

The components of the reagent kit are stored in the dark at various temperatures:

cryopreserved target cells at −70° C.

membrane dye and interleukin 2 at −20° C.

complete medium and DNA dye solution at 4° C.

BRIEF DESCRIPTION OF THE DRAWINGS

The invention is elucidated by the following examples and FIGS. 1–11.

FIG. 1 shows a flow cytometric scattered light diagram of the target cells K562.

FIG. 2 shows the setting of a live gate for dye-labelled target cells.

FIGS. 3 and 4 show flow cytometric fluorescence diagrams of target cells after an incubation period of 60 or 120 min with effectors FIG. 5 shows a fluorescence histogram of the target cells without effectors.

FIG. 6 shows a fluorescence histogram of the target cells after incubation with effectors.

FIG. 7 shows a fluorescence histogram of the target cells after incubation with effectors stimulated by interleukin 2.

FIG. 8 shows a diagram which shows the vitality of $DiOC_{18}$-labelled K562 target cells in relation to the cryopreservation period.

FIG. 10 shows a comparison of NK assays with labelled and unlabelled frozen K562 target cells and FIG. 11 shows a comparison of an NK assay according to the invention with the classical $^{51}Cr$ release assay.

EXAMPLE 1

Figure 9:
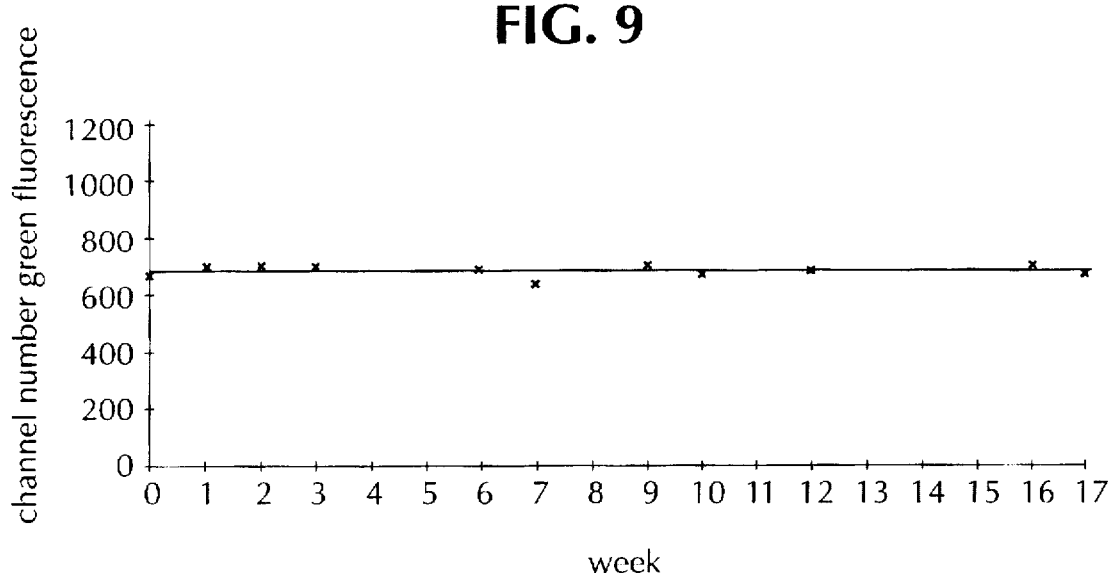
FIG. 9 shows a diagram which shows the fluorescence intensity of $DiOC_{18}$-labelled K562 target cells in relation to the cryopreservation period.

Culture and cryopreservation of the target cells K562

Material and instruments:

1. K562 target cell line (ATCC, Rockville, Md., No. CCL 243)
2. RPMI 1640 cell culture medium (Cytogen Co.)
3. foetal calf serum (FCS) (Sigma Co.)
4. cell culture flasks 225 $cm^2$ (Costar Co.)
5. dimethyl sulfoxide p.a. >99.5% (Fluka Co.)
6. freezing tubes (Costar Co.)
7. laminar-flow clean room workbench (Dan VFR 1206 Co.)
8. centrifuge (Hermle Z364 Co.)
9. 50 ml disposable centrifuge tubes (Costar Co.)

K562 cells are cultured in RPMI 1640 cell-culture medium containing 10% (v/v) FCS (complete medium) in standard cell culture flasks at 37° C. and 5% $CO_2$ in an incubator. The cells are passaged after a 48 h culture period. The doubling time of the K562 cell line is 18 h.

The freezing conditions and the use of the cells in the NK test were developed and validated for this cell line. Cells in the exponential growth phase are harvested and pelleted by centrifugation (600 rpm, 8 minutes). The cell pellet is taken up in fresh complete medium. Then the number of cells and their vitality is determined. The cell suspension is subsequently placed in an ice water bath, admixed with dimethyl sulfoxide to a final concentration of 5% (v/v) and thoroughly mixed for a brief period. The cells with a vitality >98% are aliquoted in freezing tubes at a cell concentration of $1 \times 10^6$ cells per ml. The cells are frozen at −70° C. with a temperature decrease of 1° C. per minute. The cells are stored at −70° C. in a deep freezer.

The cells stored at −70° C. retain their high vitality (>90% vital cells) over a period of at least 12 weeks. The vitality was determined with the trypan blue method. The results of 3 different freezing experiments are shown in table.

TABLE 1

| weeks after freezing the cells | vitality (%) experiment 1 | vitality (%) experiment 2 | vitality (%) experiment 3 |
| --- | --- | --- | --- |
| before freezing | 98 | 99 | 99 |
| 1 | 97 | 98 | 99 |
| 2 | 97 | 98 | 99 |
| 3 | 95 | 98 | 97 |
| 4 | 95 | 97 | 97 |
| 5 |  | 98 | 96 |
| 6 | 96 | 97 | 96 |
| 7 | 96 | 97 | 96 |
| 8 | 94 | 96 |  |
| 9 | 95 | 96 |  |
| 10 | 93 |  |  |
| 11 |  |  | 93 |
| 12 |  |  | 94 |
| 13 |  | 95 |  |
| 14 |  | 95 |  |
| 16 |  | 95 | 93 |
| 18 |  | 94 |  |

EXAMPLE 2

Determination of the NK activity of human peripheral blood lymphocytes (PBLs)

Material and instruments 1. refrigerated centrifuge with free-swinging inserts (e.g. Hermle centrifuge ZK 364)
2. water-bath (GFL Co., type 1083)
3. laminar flow clean room workbench
4. vortex mixer (Vortex-Genie, model K-550-GE)
5. Neubauer counter chamber with cover glass
6. variable transfer pipettes
7. flow cytometer with an excitation wavelength of 488 nm (e.g. FACScan, Becton Dickinson)
8. 5 ml Falcon sample tubes (12×75 mm, Becton Dickinson) with stoppers
9. EDTA ($K_3$) blood collection tubes (e.g. Becton Dickinson)
10. LeucoPrep 13 or 16 mm cell separation tubes (Becton Dickinson) or Isopaque-Ficoll (Histopaque®, Sigma, or Ficoll Paque®, Pharmacia) for the preparation of mononuclear cells
11. 15 ml disposable centrifuge tubes (e.g. Falcon or Costar)
12. 50 ml disposable centrifuge tubes (e.g. Costar)
13. sterile PBS or physiological saline solution
14. ice bath with cover
15. pipette tips
16. cryopreserved target cells K562 as described in example 1
17. RPMI 1640 cell culture medium (Cytogen Co.)
18. foetal calf serum (FCS) (Sigma Co.)
19. propidium iodide (Sigma Co.)
20. membrane dye $DiOC_{18}$ (Molecular Probes Co.)

Effector cells are obtained from 5–10 ml citrate blood, EDTA blood or heparin blood by density gradient centrifugation (LeukoPREP cell separation tubes or Ficoll-Hypaque). The isolated mononuclear cells are subsequently adjusted to a cell concentration of $5 \times 10^6$ cells/ml complete medium.

Ca. 50 ml complete medium is placed in a 50 ml centrifuge tube and prewarmed in a water bath to 37° C. The K562 cells stored at −70° C. are rapidly thawed in a water bath i.e.

within 2 min and immediately transferred into the 50 ml centrifuge tube containing the medium. The tube is briefly swirled and centrifuged (120×g, 2–3 min). The cells are washed once with 15 ml complete medium (120×g, 2–3 min).

The medium is subsequently removed, the cells are resuspended in 5 ml complete medium. After addition of 20 µl of the membrane dye $DiOC_{18}$ (1.4 mM) and an immediate brief vortex mixing, the cell suspension is incubated for 15 min at 37° C. in a water bath. Subsequently 10 ml complete medium is added and it is centrifuged (120×g, 2–3 min). The cells are taken up in 1 ml medium and adjusted to a cell concentration of $1\times10^5$/ml.

Depending on the desired ratio of effectors to target cells, the following cell mixtures were prepared by pipetting them together into a centrifuge tube with a snap cap.

| Ratio E:T | Effectors (µl) | Target cells (µl) | Complete medium |
| --- | --- | --- | --- |
| 50:1 | 100 | 100 | 0 |
| 25:1 | 50 | 100 | 50 |
| 12.5:1 | 25 | 100 | 75 |

It is recommended to carry out duplicate determinations in each case. A preparation to which effectors have not been added serves as a control in order to determine the spontaneous death rate of the target cells. Preparations to which 30 µl interleukin 2 (=30 U/ml, 6 U/preparation) has been added in each case serve as a positive control and in this case the effector cells do not have to be preincubated with IL-2.

The centrifuge tubes are briefly centrifuged (100 g, 1 min). The preparations are incubated in a water bath at 37° C. in centrifuge tubes on which snap caps have been placed. After an incubation period of 30, 60, 120 or 240 min the samples are placed in an ice water bath, each is admixed with 50 µl DNA dye solution (40 µg/ml propidium iodide), briefly mixed by vortexing and analysed after 10 min by flow cytometry.

In order to be able to determine a significant NK activity an incubation period of 120 min is recommended.

The evaluation is carried out in a flow cytometer (e.g. FACScan) using commercial software (e.g. LYSIS II). The fluorescence signals are collected in the case of green fluorescence (DiOC) through a 530/30 nm bandpass filter, in the case of red fluorescence (propidium iodide) either through a 585 nm bandpass or a >650 nm longpass filter. The fluorescence parameters are amplified logarithmically (4 decades), the light scattering parameters (forwards and side light scattering) are amplified linearly. The scattered light diagram of the target cells K562 is shown in FIG. 1.

It is essential for the flow cytometric analysis of the cytotoxicity to be able to differentiate target cells from effector cells. For this purpose only green fluorescent target cells are registered by placing a live gate (FIG. 2).

FIGS. 3 and 4 show the FL3/FL1-dot plot analyses of the target cells after an incubation period of 60 or 120 min with effectors.

The number of dead i.e. red fluorescent target cells is evaluated. The percentage of cytotoxicity is calculated by subtracting the percentage of dead cells in the sample with target cells alone without effectors (FIG. 5 in the example 2.4%) from the percentage of dead target cells in the test mixtures with added effectors (FIG. 6 in the example 40.9%). A histogram of the FL3 fluorescence of target cells is shown in FIG. 7 after a 120 min incubation with effectors with addition of 30 U/ml interleukin 2. In this case the percentage of dead target cells was 81.5%.

EXAMPLE 3
Cryopreservation of labelled target cells

K562 target cells were harvested in the log phase and adjusted to a concentration of $2\times10^6$/ml in complete medium. For the labelling with the lipophilic membrane dye $DiOC_{18}$, 20 µl of the stock solution (1.42 nM in DSMO) was added to 5 ml of the target cell suspension in complete medium. The cells were incubated for 15 min. at 37° C., washed once with complete medium (120 g, 3 min) and subsequently again incubated for 4–6 h in an incubator. Then the dyed target cells were frozen as described for the undyed cells and stored at −70° C. while retaining their vitality.

FIG. 8 shows a diagram in which the vitality of labelled frozen K562 target cells is shown in relation to the cryopreservation period. It can be seen that even after a cryopreservation period of 17 weeks the vitality is still surprisingly >90%.

FIG. 9 shows a diagram which shows the fluorescence intensity of labelled frozen K562 target cells relative to the cryopreservation period. It can be seen that the green fluorescence has a high stability and even after a long cryopreservation period there is no significant change.

Figure 10:
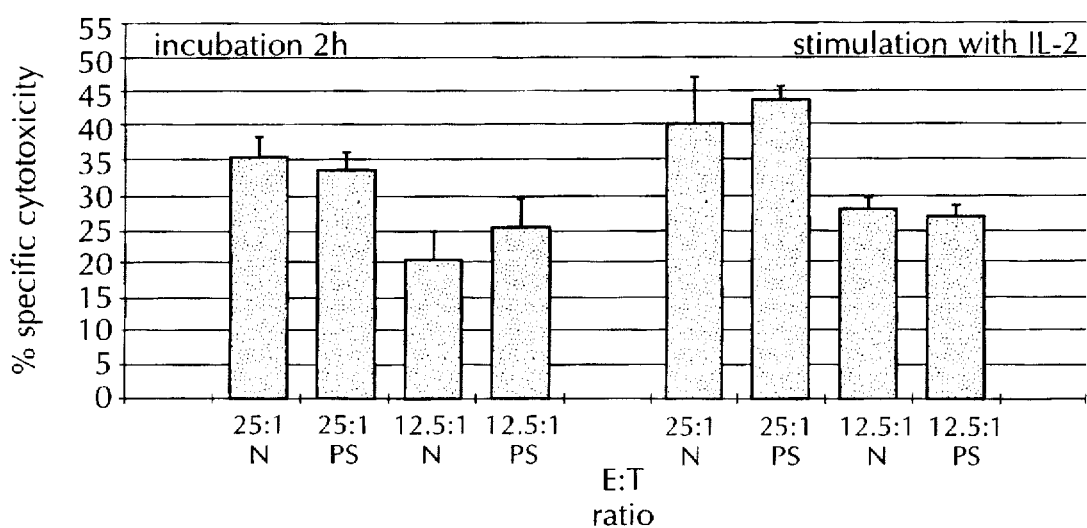

Labelled frozen K562 target cells were compared in an NK assay with target cells which had not been labelled with the lipophilic membrane dye $DiOC_{18}$ until after thawing. This comparison is shown in FIG. 10. Labelled (PS) and unlabelled (N) frozen K562 cells were used in a ratio of effector cells (E) to target cells (T) of 25:1 and 12.5:1. The test was carried out by incubating the effector and target cells for 2 hours without or with stimulation with IL-2. As can be seen from FIG. 10 there was no statistically significant difference between the labelled and unlabelled frozen target cells with regard to the specific cytotoxicity.

EXAMPLE 4
Comparison of the method according to the invention with the classical $^{51}Cr$ release assay The method according to the invention was compared with the classical $^{51}Cr$ release assay. For this a total of 25 parallel determinations at three different ratios of effector to target cells (50:1, 25:1 and 12.5:1) were carried out. The incubation in each case was 4 hours. The results of this comparison are shown in FIG. 11. As can be seen from this figure the new method is comparable to the old with regard to precision but is much more rapid.

We claim:

1. A method for determining the action of effectors on target cells, wherein said target cells are thawed cryopreserved mammalian cells which have a vitality of at least 90% after storage at −70° C. for a period of 4 weeks and which have not previously been cultured with said effectors wherein said cryopreserved mammalian cells are prepared by suspending mammalian target cells in a medium, labeling said mammalian cells, culturing said cells for 4–6 hours, adding a cryopreservative up to a final concentration of 2–10% (v/v) and freezing the cells with a vitality of >98% by decreasing the temperature at a rate of no more than 2° C. per minute.

2. The method as claimed in claim 1, wherein said target cells are derived from a cell culture.

3. The method as claimed in claim 1, wherein the medium contains the cryopreservative at a final concentration of 4–8% (v/v).

4. The method as claimed in claim 1, wherein the cryopreservative is dimethyl sulfoxide.

5. The method as claimed in claim 1, wherein the rate of temperature decrease is 0.5–1.5° C. per minute.

6. The method as claimed in claim 1, wherein the cryopreserved cells have a vitality of at least 90% after storage at −70° C. for a period of 12 weeks.

7. The method as claimed in claim 1, wherein the mammalian cells are a human cell line.

8. The method as claimed in claim 7, wherein the human cell line is a human tumor or leukemia cell line.

9. The method as claimed in claim 8, wherein the human cell line is selected from the group consisting of chronic myelogenic leukemia cell line K562 (ATCC CCL 243), acute lymphoblastic leukemia T cell line MOLT-4, acute promyelocytic leukemia cell line HL-60, ovarian carcinoma cell line Goodwin and alveolar cell carcinoma cell line A 549.

10. The method as claimed in claim 1, wherein the effector is a natural killer (NK) cell.

11. The method as claimed in claim 10, wherein the suspended mammalian cells are labelled with a first marker substance before cryopreservation, the labeled target cells are mixed and incubated with a sample containing NK cells, a second marker substance, which is specific for killed target cells, is added to the cell mixture and the presence of target cells labelled with said second marker is determined.

12. The method as claimed in claim 1, wherein the target cells are labelled with a membrane specific dye.

13. The method as claimed in claim 12, wherein the membrane dye is a 3,3'-dioctadecyloxacarbocyanine or a salt thereof.

14. The method as claimed in claim 11, wherein the sample containing the NK cells is a preparation of peripheral mononuclear blood cells that have been isolated by density gradient centrifugation.

15. The method as claimed in claim 11, wherein the second marker substance is a DNA dye.

16. The method as claimed in claim 15, wherein the DNA dye is propidium iodide.

17. The method as claimed in claim 1, wherein several determinations are carried out in parallel with different ratios of effectors to target cells.

18. The method as claimed in claim 1, wherein several determinations are carried out in parallel in the presence and absence of effector modulators.

19. A reagent kit for the determination of the activity of natural killer cells (NK cells), wherein said kit comprises (a) cryopreserved mammalian cells labelled with a membrane dye said cryopreserved cells having a vitality of at least 90% after thawing and (b) a sample of a DNA dye.

20. The kit as claimed in claim 19, further comprising at least one of a medium or a modulator for NK cells.

21. The method of claim 12, wherein the membrane specific dye is a lipophilic fluorescent dye.

22. The method of claim 15, wherein said DNA dye is a fluorescent dye.

* * * * *

UNITED STATES PATENT AND TRADEMARK OFFICE
CERTIFICATE OF CORRECTION

PATENT NO. : 5,902,733
DATED : May 11, 1999
INVENTOR(S) : Werner Hirt, et al.

It is certified that error appears in the above-identified patent and that said Letters Patent is hereby corrected as shown below:

In column 2, line 38, insert a space between "A" and "549" to read as
-- A 549 --.

In column 2, line 44, change "1x105" to -- $1 \times 10^5$ --.

In column 5, line 1, insert a dash before the word "cryopreserved" to read as
-- – cryopreserved --.
In column 5, line 2, insert a dash before the word "membrane" to read as
-- – membrane --.
In column 5, line 3, insert a dash before the word "complete" to read as
-- – complete --.

Signed and Sealed this

Thirty-first Day of October, 2000

Attest:

Q. TODD DICKINSON

*Attesting Officer*  *Director of Patents and Trademarks*